United States Patent
Anderson et al.

(10) Patent No.: US 9,155,482 B2
(45) Date of Patent: Oct. 13, 2015

(54) APPARATUS AND METHOD FOR INDICATING CARDIAC OUTPUT

(75) Inventors: John McCune Anderson, Holywood (GB); Cesar Oswaldo Navarro-Paredes, Newtownabbey (GB); Rebecca DiMaio, Belfast (GB)

(73) Assignee: Heartsine Technologies Limited, Belfast Antrim (GB)

(*) Notice: Subject to any disclaimer, the term of this patent is extended or adjusted under 35 U.S.C. 154(b) by 543 days.

(21) Appl. No.: 12/920,708

(22) PCT Filed: Mar. 4, 2009

(86) PCT No.: PCT/EP2009/052539
§ 371 (c)(1),
(2), (4) Date: Sep. 2, 2010

(87) PCT Pub. No.: WO2009/109595
PCT Pub. Date: Sep. 11, 2009

(65) Prior Publication Data
US 2011/0021938 A1    Jan. 27, 2011

(30) Foreign Application Priority Data

Mar. 5, 2008   (IE) .................................. S2008/0163
Sep. 26, 2008  (IE) .................................. S2008/0785

(51) Int. Cl.
A61B 5/05    (2006.01)
A61B 5/029   (2006.01)
A61B 5/053   (2006.01)
A61N 1/39    (2006.01)

(52) U.S. Cl.
CPC .............. *A61B 5/029* (2013.01); *A61B 5/0535* (2013.01); *A61N 1/39* (2013.01); *A61N 1/3925* (2013.01)

(58) Field of Classification Search
USPC ....................................... 600/513, 526; 607/5
See application file for complete search history.

(56) References Cited

U.S. PATENT DOCUMENTS

| | | | |
|---|---|---|---|
| 8,262,581 B2* | 9/2012 | Uemura et al. | 600/526 |
| 8,290,577 B2* | 10/2012 | Brooks et al. | 600/513 |
| 2003/0109790 A1* | 6/2003 | Stickney et al. | 600/500 |
| 2004/0116969 A1 | 6/2004 | Owen et al. | |

FOREIGN PATENT DOCUMENTS

| | | |
|---|---|---|
| WO | WO 2006/003243 A1 | 1/2006 |
| WO | WO 2006/005557 A1 | 1/2006 |
| WO | WO 2007/134143 A2 | 11/2007 |

OTHER PUBLICATIONS

Saeed et al. "Multiparameter Trend Monitoring and Intelligent Displays Using Wavelet Analysis" Computers in Cardiology. 2000, 27:797-800.*

* cited by examiner

*Primary Examiner* — Paula J Stice
(74) *Attorney, Agent, or Firm* — Novak Druce Connolly Bove + Quigg LLP

(57) ABSTRACT

An apparatus for indicating cardiac output comprises means for monitoring a patient's transthoracic impedance and generating a corresponding impedance signal, and signal processing means for (a) deriving a signal S1 which is a measure of the average amplitude of the impedance signal, (b) filtering the impedance signal at a plurality of different wavelengths within a predetermined frequency band, (c) for each filter deriving a signal S2 which is a measure of the average amplitude of the respective filter output, (d) calculating the ratio of the maximum one of the signals S2 derived from step (c) to the signal S1 derived from step (a), and (e) using the ratio from step (d) in a decision tree to provide a signal indicating cardiac output or not.

16 Claims, 2 Drawing Sheets

APPARATUS AND METHOD FOR INDICATING CARDIAC OUTPUT

FIELD OF THE INVENTION

This invention relates to an apparatus and method for indicating cardiac output in a cardiac arrest patient.

BACKGROUND TO THE INVENTION

Formerly, first responders had been advised to check suspected cardiac arrest victims for a pulse. However, the accurate determination of a pulse has been shown to be poor and the time taken far exceeded the value of the determination. For this reason, lay responders are advised not to administer pulse checks in accordance with European and US Guidelines. If a patient presents with ventricular fibrillation, a pulseless arrhythmia, defibrillation is required immediately. However, if a pulse is present during an episode of High Rate Ventricular Tachycardia (HRVT), then it is possible that a shock might not be the most appropriate therapy.

It is therefore becoming essential that lay persons using public access defibrillators are provided a more reliable means of determining if there is a pulse. Such a means is provided by the measurement of the impedance electrocardiogram—the resistance of the body to the passage of electricity. The impedance Z, as well as its first derivative (dZ/dt), has been shown have direct correlation to arterial blood flow. Herein, the term ICG will mean the first derivative of the patient impedance Z, if necessary after conditioning and filtering.

PRIOR ART

Markers for cardiac output can be obtained from the frequency components of the ICG. These frequency components can be derived by Fast Fourier Analysis of the ICG signal. However, the accuracy and value of these markers depends on the ability to perform the FFT. Fast Fourier Transformation of an ICG can take a long time and consumes considerable processor capacity. In emergency resuscitation situations, this is a major problem when fast, real-time diagnosis can be essential to the survival of a patient.

SUMMARY OF THE INVENTION

According to an aspect of the present invention, there is provided an apparatus as specified in claim 1.

According to another aspect of the present invention, there is provided a method as specified in claim 9.

The invention provides an apparatus for indicating cardiac output, comprising means for monitoring a patient's transthoracic impedance and generating a corresponding impedance signal, and signal processing means for performing the following steps:
a. deriving a signal (herein referred to as S1) which is a measure of the average amplitude of the impedance signal,
b. filtering the impedance signal at a plurality of different wavelengths within a predetermined frequency band,
c. for each filter deriving a signal (herein referred to as S2) which is a measure of the average amplitude of the respective filter output,
d. calculating the ratio of the maximum one of the signals S2 derived from step c to the signal S1 derived from step a, and
e. using the ratio from step d to provide a signal indicating cardiac output or not.

The impedance signal may be the patient's ICG or the undifferentiated patient impedance.

Preferably the signal S1 is derived by calculating the RMS of the impedance signal, and each signal S2 is derived by calculating the RMS of the respective filter output.

Most preferably, the apparatus forms part of an automated external defibrillator including patient electrodes for both applying a shock to the patient and obtaining the patient's transthoracic impedance.

An embodiment of the present invention discloses a system incorporated into an automated external defibrillator which measures the impedance of a patient using only the two defibrillator electrodes and establishes, using an algorithm, a marker for cardiac arrest. This marker can then be used, in conjunction with the defibrillator's own diagnostic algorithm, to even more accurately determine whether or not the presented rhythm is shockable.

The invention teaches that a filtering technique, specifically, integer filtering, can be used to simulate the FFT process and extract a marker for cardiac output. This is particularly useful since it is unlikely that there will be sufficient time, or processor capacity, to perform FFT on the impedance signal in the time required for diagnosis in a portable and low cost defibrillator. The use of the present technique has been shown to increase significantly the specificity of the determination of cardiac output by first responders.

The invention is also directed to a method by which the described apparatus operates and including method steps for carrying out every function of the apparatus.

DESCRIPTION OF AN EMBODIMENT OF THE INVENTION

Figure 1:
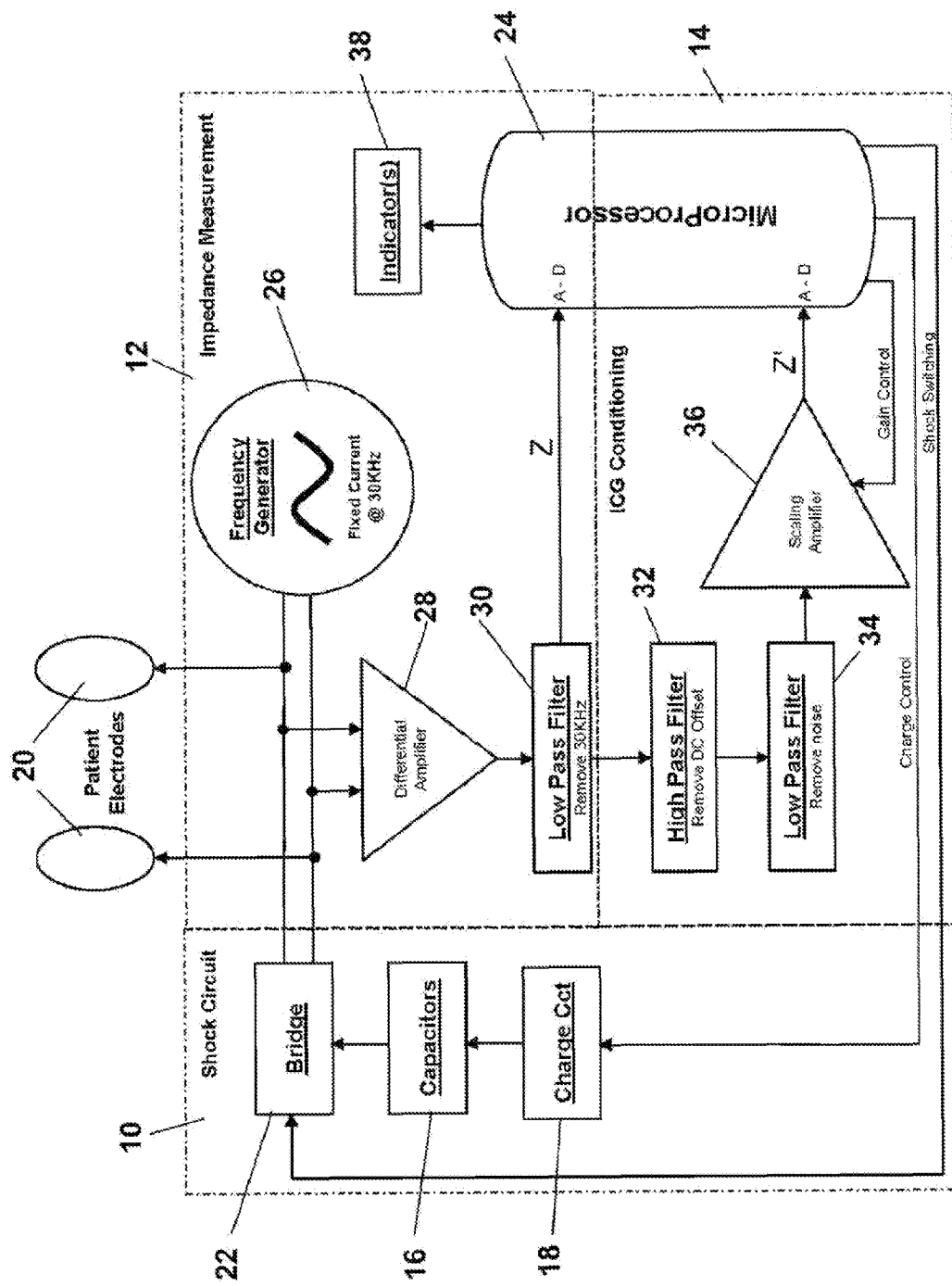
FIG. 1 is a block diagram of an automated external defibrillator incorporating an embodiment of the invention.

Referring to FIG. 1 of the drawings, an automated external defibrillator comprises three main sections: 10, 12 and 14.

Section 10 is the main high voltage shock circuitry and comprises a bank of capacitors 16 which are charged up to a high voltage by a charging circuit 18, the charge being released as a bi-phasic high voltage shock through a pair of patient electrodes 20 by a bridge circuit 22. The charging of the capacitors 16 and the shape and duration of the bi-phasic shock waveform is controlled by a microprocessor 24, the actual shock being given by the user pressing a button if the patient's condition is deemed "shockable" as determined by a diagnostic algorithm having the patient's ECG and ICG as inputs. The ECG is derived in known manner (not shown). The process is prompted by voice messages and/or visual prompts output on visual/audio indicators 38 (the indicators are shown in section 12 for diagrammatic simplicity). The audio/visual output indicators 38 may comprise a loudspeaker and/or LED(s). Section 12 measures the patient's transthoracic impedance using the same electrodes 20 as are used for applying the shock. A generator 26 produces a 30 kilohertz sinusoidal waveform at a constant current of 100 microamperes. This signal is applied across the electrodes 20. When the electrodes are attached to a patient, a voltage across the electrodes is generated which is superimposed on the 30 kHz sinusoid. This voltage is a direct measurement of the transthoracic impedance of the patient. The voltage generated in response to the sinusoid is applied to a differential amplifier 28 which converts it from a differential signal to a single signal referenced to ground potential. The resultant waveform is passed through a low pass filter 30 which removes the original 30 kHz signal leaving a signal Z which is directly proportional to the patient impedance. The signal Z is used by the microprocessor 24 to set the bi-phasic pulse amplitude and width to ensure that the correct total energy (typically 150 Joules) is delivered to the patient.

The construction and operation of sections 10 and 12 of the AED are well-known in themselves, and it is not thought that further detail is necessary.

Section 14 provides for the further conditioning of the signal Z in preparation for differentiation by the microprocessor 24, and is additional to the existing circuitry for the measurement of patient impedance, section 12. In section 14 of the defibrillator the signal Z from the low pass filter 30 is passed through a high pass filter 32 which removes the dc offset before removing higher frequency noise in the low pass filter 34. Finally the signal is scaled in an amplifier 36 incorporating digital gain control to a level appropriate for analogue-to-digital conversion by the microprocessor 24. The result is a signal Z' which differs from the signal Z in respect of filtering and amplification, but is still a measure of the patient's transthoracic impedance.

Figure 2:
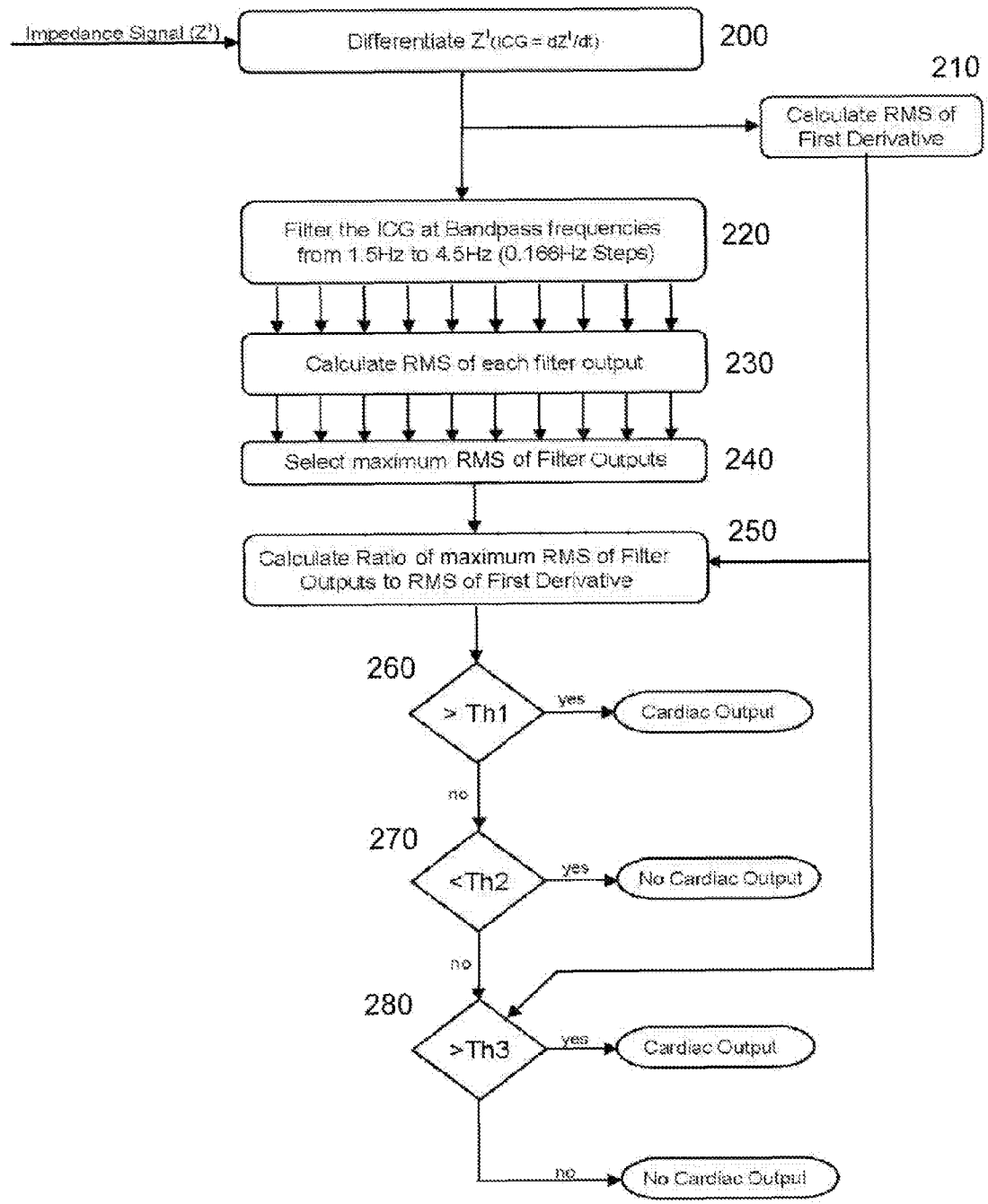
FIG. 2 is a flow diagram of a process, performed in software by the microprocessor in FIG. 1, for determining cardiac output.

FIG. 2 is a flow diagram of a process for determining cardiac output, which performed in software by the microprocessor 24. Basically, the process identifies the main frequency component of the patient's ICG by filtering, and thence establishes the presence or otherwise of cardiac output. The ranges and threshold values used in this embodiment were obtained empirically by analysing a large volume of patient data to establish the relationship between cardiac output and the patient's ICG using only two electrodes on patients presenting with a normal sinus rhythm.

a. At step 200 the signal Z' is digitally converted, conditioned and differentiated by software in the microprocessor 24 to derive the (digital) ICG.

b. At step 210 the root mean square (RMS) of the ICG is calculated over a predetermined period which is four seconds in this embodiment but is typically from 1-12 seconds.

c. Next, step 220, the ICG is filtered at a plurality of different wavelengths within a predetermined frequency band. In this embodiment the frequency band is from 1 Hz to 4.5 Hz and the ICG is filtered at a plurality of different frequencies spaced at intervals of 0.166 Hz. In general the frequency band may be from 1-5 Hz and is preferably filtered at least six frequencies within that band. At each frequency the signal is filtered in a very narrow band centred on the respective frequency.

d. At step 230 the RMS of each filter output is calculated, preferably over the same period as the RMS in step 210, i.e. four seconds in this embodiment.

e. Next, step 240, that filter output whose RMS is a maximum is selected.

f. At step 250 the ratio of the maximum RMS (from step 240) to the RMS of the original ICG (from step 210) is calculated. This will normally be a number between 0 and 1, depending on how closely the average amplitude of the selected filter output matches the average amplitude of the original ICG over the selected four-second period. This ratio is now used in a decision tree comprising steps 260 to 280 to provide a signal indicating cardiac output or not.

h. In step 260 the ratio is compared with a first threshold Th1 which is typically 0.75. If the ratio exceeds the threshold Th1 a signal indicating cardiac output is generated.

i. If the ratio is not greater than Th1, it is compared in step 270 with a second, lower threshold Th2 which is typically 0.25. If the ratio is less than the threshold Th2 a signal indicating no cardiac output is generated.

j. If the ratio falls between the two thresholds Th1 and Th2 a third comparison is made to ensure that the RMS of the ICG is sufficiently high. Thus, step 280, if the ratio lies between Th1 and Th2, the RMS of the original ICG is compared with a third threshold Th3. If the RMS exceeds the threshold Th3 a signal indicating cardiac output is generated, whereas if the RMS is less than the threshold Th3 a signal indicating no cardiac output is generated. The experimental value of Th3 used in this embodiment is 0.136 ohms/sec. However adjustments to the thresholds Th1, Th2 and Th3 around their typical values may be applied.

The output of the decision tree, i.e. cardiac output/no cardiac output, is used as a further input to the diagnostic algorithm in addition to the patient's ECG. This provides a further refinement of the algorithm, for example, if the patient is judged by the algorithm to be in ventricular tachycardia (VT). Some forms of this are shockable, others not. Using the above algorithm, the ICG can be used to determine if, while in VT, there is cardiac output. If not, the patient can be shocked accordingly.

Although the RMS of the ICG and filter outputs have been used in steps b and d above, other methods of measuring the average amplitude of the signals can be used, such as average peak-to-peak measurement.

In an alternative embodiment of the invention, steps 210 to 280 of the above process operate on the undifferentiated signal Z' rather than the differentiated ICG. In other words, step 200 of the process is omitted and Z' (after further filtering to minimise the effect of respiration and noise, especially noise due to the capacitor charging process) is applied directly to process steps 210 and 220. Therefore, in this alternative embodiment, references to the ICG in the above process description are replaced by references to the undifferentiated signal. In addition, the thresholds are changed to typical values as follows: Th1=0.48, Th2=0.03 and Th3=0.0466 ohms.

Whilst the invention has been embodied in an automated external defibrillator, it is possible that a stand-alone cardiac output indicator could be made according to the principles of the present invention, i.e. independent of a defibrillator.

The invention is not limited to the embodiments described herein which may be modified or varied without departing from the scope of the invention.

The invention claimed is:

1. An external defibrillator, comprising:
    a processor;
    a frequency generator;
    a pair of electrodes; and
    a non-transitory computer-readable storage medium having instructions stored which, when executed by the processor, cause the processor to perform operations comprising:
        signaling the frequency generator to generate an impedance test signal;
        when the pair of electrodes are in contact with a patient, applying the impedance test signal to the patient via the pair of electrodes;
        receiving an impedance measurement in response to the impedance test signal; repeating the impedance test signal with the patient to acquire a plurality of impedance measurements;
        averaging the plurality of impedance measurements over a defined period of time, to yield an average impedance measurements;
        filtering each of the plurality of impedance measurements at a plurality of different spaced frequencies within a predetermined band, to yield a plurality of filtered impedance measurements;

averaging each of the plurality of filtered impedance measurements over a defined period of time, to yield a plurality of average filtered impedance measurements;

identifying a maximum average filtered impedance measurement from the plurality of average filtered impedance measurements;

calculating a ratio of the maximum average filtered impedance measurement to the average impedance measurement;

comparing the calculated ratio with a predetermined threshold value to provide a signal indicating the presence or absence of a cardiac output; and providing the signal indicating the presence or absence of the cardiac output to a user.

2. The external defibrillator of claim 1,
wherein the threshold value is in a range inclusively comprising 0.25 to 0.75; and
when the calculated ratio exceeds the threshold value, a first signal is provided indicating the presence of a cardiac output; and
when the calculated ratio is below the threshold value, a second signal is provided indicating the absence of a cardiac output.

3. The external defibrillator of claim 2, the computer-readable storage medium having additional instructions stored which, when executed by the processor, result in operations, comprising:
when the calculated ratio is below the first threshold value, comparing the calculated ratio with a second threshold value that is lower than the first threshold value; and
when the calculated ratio is less than the second threshold value, providing a distinct signal indicating the absence of a cardiac output.

4. The external defibrillator of claim 3, wherein the second threshold value is in a range inclusively comprising 0.25 to 0.03.

5. The external defibrillator of claim 1, wherein the defined period of time is in a range inclusively comprising 1-12 seconds.

6. The external defibrillator of claim 1, wherein the predetermined frequency band has a bandwidth in a range inclusively comprising 1 to 5 Hz.

7. The external defibrillator of claim 6, wherein the plurality of different spaced frequencies number at least 6 distinct frequencies within the predetermined frequency band.

8. The external defibrillator of claim 6, wherein the plurality of different spaced frequencies are consecutively grouped at intervals of a least 0.166 Hz.

9. A method for use with an external defibrillator, comprising:
signaling a frequency generator to generate an impedance test signal;
when a pair of electrodes are in contact with a patient, applying the impedance test signal to the patient via the pair of electrodes;
receiving an impedance measurements in response to the impedance test signal;
repeating the impedance test signal with the patient to acquire a plurality of impedance measurements;
averaging the plurality of impedance measurements over a defined period of time, to yield an average impedance measurements;
filtering each of the impedance measurements at a plurality of different spaced frequencies within a predetermined frequency band, to yield a plurality impedance measurements;
averaging each of the plurality of filtered impedance measurements over a defined period of time, to yield a plurality of average filtered impedance measurements;
indentifying a maximum average filtered impedance measurement from the plurality of average filtered impedance measurements;
calculating a ratio of the maximum average filtered impedance measurement to the average impedance measurement;
comparing the calculated ratio with a predetermined threshold value to provide a signal indicating the presence or absence of a cardiac output; and providing the signal indicating the presence or absence of the cardiac output to a user.

10. A method of claim 9, wherein the threshold value is in a range inclusively comprising 0.25 to 0.75; and
when the calculated ratio exceeds the threshold value, a first signal is provided indicating the presence of a cardiac output; and
when the calculated ratio is below the first threshold value, a second signal is provided indicating the absence of a cardiac output.

11. The method of claim 10, comprising:
when the calculated ratio is below the first threshold value, comparing the calculated ratio with a second threshold value that is lower than the first threshold value; and
when the calculated ratio is less than the second threshold value, providing a signal indicating the absence of a cardiac output.

12. A method of claim 11, wherein the second threshold value is in range inclusively comprising 0.25 to 0.30.

13. The method of claim 9, wherein the defined period of time is in a range inclusively comprising 1-12 seconds.

14. The method of claim 9, wherein the predetermined frequency band has a bandwidth in a range inclusively comprising 1 to 5 Hz.

15. The method of claim 9, wherein the plurality of different spaced frequencies number at least six distinct frequencies in the predetermined frequency band.

16. The method of claim 9, wherein the plurality of different spaced frequencies are consecutively grouped at intervals of at least 0.166 Hz.

* * * * *